(12) United States Patent
Koshiji

(10) Patent No.: US 7,667,657 B2
(45) Date of Patent: Feb. 23, 2010

(54) INFORMATION PROCESSING APPARATUS

(75) Inventor: Fukuro Koshiji, Hachioji (JP)

(73) Assignee: Konica Minolta Holdings, Inc., Tokyo (JP)

( * ) Notice: Subject to any disclaimer, the term of this patent is extended or adjusted under 35 U.S.C. 154(b) by 273 days.

(21) Appl. No.: 11/791,621

(22) PCT Filed: Nov. 4, 2005

(86) PCT No.: PCT/JP2005/020266

§ 371 (c)(1),
(2), (4) Date: May 25, 2007

(87) PCT Pub. No.: WO2006/059454

PCT Pub. Date: Jun. 8, 2006

(65) Prior Publication Data

US 2008/0129621 A1    Jun. 5, 2008

(30) Foreign Application Priority Data

Nov. 30, 2004 (JP) .............................. 2004-345579

(51) Int. Cl.
*H01Q 1/12* (2006.01)
*H01Q 11/12* (2006.01)
*H01Q 9/16* (2006.01)

(52) U.S. Cl. .................. 343/718; 343/741; 343/793
(58) Field of Classification Search .................. 343/718, 343/741, 793, 872, 702, 878, 893
See application file for complete search history.

(56) References Cited

U.S. PATENT DOCUMENTS

| 5,572,488 | A  | * | 11/1996 | Yamada et al. ............. 368/10 |
| 6,335,906 | B1 | * | 1/2002  | Engelmann ................ 368/10 |
| 6,359,837 | B1 | * | 3/2002  | Tsukamoto ................ 368/10 |
| 7,187,908 | B2 | * | 3/2007  | Fujisawa et al. ............ 455/88 |

FOREIGN PATENT DOCUMENTS

| JP | 7-170215   | A | 7/1995  |
| JP | 7-283632   | A | 10/1995 |
| JP | 8-330826   | A | 12/1996 |
| JP | 10-155749  | A | 6/1998  |
| JP | 2003-24285 | A | 1/2003  |
| JP | 2003-37566 | A | 2/2003  |

* cited by examiner

*Primary Examiner*—Shih-Chao Chen
(74) *Attorney, Agent, or Firm*—Frishauf, Holtz, Goodman & Chick, P.C.

(57) ABSTRACT

The subject is to provide an information processing apparatus serving as a wearable device, which makes it possible not only to reduce the divergence of data toward the peripheral spaces, but also to eliminate the electrode to be contacted to the surface of the living body when wearing it, and further, which is superior in the transmitting efficiency. The information processing apparatus is provided with information processing section 101 to conduct various kinds of information processing; wearing section 170 to make the information processing section wearable onto a living body, by surrounding a part of the living body; antenna section 180 formed in the wearing section and serving as either a loop antenna or a dipole antenna; and communicating section 160 to conduct a wireless communication with an external device by transmitting data, processed by the information processing section, to the external device through the antenna section, or by feeding data, received from the external device through the antenna section, into the information processing section.

4 Claims, 12 Drawing Sheets

INFORMATION PROCESSING APPARATUS

This application is a U.S. National Phase Application under 35 Usc 371 of International Application PCT/JP2005/020266 filed Nov. 4, 2005.

FIELD OF THE INVENTION

The present invention relates to an information processing apparatus for conducting various kinds of information processing operations, and specifically relates to an information processing apparatus, which serve as a wearable device provided with a wearing section for surrounding a part of a living body.

TECHNICAL BACKGROUND

There has been proposed that a small sized computer device is fitted on a part of the living body as a wearable device. Further, it has been also proposed that wireless communications between the above wearable device and other wearable devices or other stationary devices are conducted, while wearing the wearable device on the part of the living body.

Generally speaking, a wireless communication, an infrared communication, etc. has been employed as the communicating method to be conducted by such the wearable device. When employing such the wireless communication, divergences of the electro-magnetic waves into the surrounding space are liable to cause a leakage of data to be communicated, resulting in a problem of degradation of its security level.

To overcome such the problem, it is expected, from a security point of view, that a safer method be employed for transmitting the information. For instance, Patent Document 1 and Patent Document 2, both indicated below, set forth a technology that the transmitter contacting the living body transmits the information to the receiver through the living body.

[Patent Document 1]
Tokkaihei 7-170215, (Page 1, FIG. 1, Japanese Non-Examined Patent Publication)
[Patent Document 2]
Tokkai 2003-37566, (Page 1, FIG. 1, Japanese Non-Examined Patent Publication)

DISCLOSURE OF THE INVENTION

Subject to be Solved by the Invention

In the information transmitting system disclosed by Patent Document 1 and Patent Document 2 cited in the above, by contacting the electrode onto the surface of the living body (namely, the skin of the human body), the living body itself is utilized as the transmission path for transmitting the information through the electrode.

Accordingly, the divergence or leakage of the data toward the peripheral spaces could be reduced to a lower level, and the security of such the information transmitting system can be considered as a higher level, compared to such the conventional type system in which the electro-magnetic waves are emitted from the antenna exposed in the air.

The conventional type system, however, still has a problem that the communication cannot be achieved without contacting the electrode onto the surface of the living body (namely, the skin of the human body). Accordingly, it has been antici- pated that it becomes difficult to wear the wearable device, depending on a way of dressing.

Further, since a metal directly contacts the living body, the problems in regard to Allergies and sanitary aspects would possibly arise.

Still further, since the living body serves as a conductive material in respect to the electrode and also serves as a transmission path in the closed circuit, there also arise another problem that the transmitting efficiency is getting worse. In addition, since the contact resistance may vary depending on a state of the surface of the living body (dry or wet), and since the coupling condition (electrostatic coupling) may also vary depending on the change of peripheral environment, etc., there also arise still another problem that the transmission characteristics would be deteriorated, and therefore, the performance of the conventional type system cannot be stabilized.

To overcome the abovementioned drawbacks in conventional information processing apparatus, it is one of objects of the present invention to provide an information processing apparatus serving as a wearable device, which makes it possible not only to reduce the divergence of data toward the peripheral spaces, but also to eliminate the electrode to be contacted to the surface of the living body when wearing it, and further, which is superior in the transmitting efficiency.

Accordingly, at least one of the objects of the present invention can be attained by the information processing apparatus described as follows.

According to an information processing apparatus reflecting an aspect of the present invention, the information processing apparatus, comprises: an information processing section to conduct various kinds of information processing; a wearing section to surround a part of a living body, so as to make the information processing section wearable onto the living body; an antenna section that serves as either a loop antenna or a dipole antenna, integrally formed in the wearing section; and a communicating section to transmit data, processed in the information processing section, to an external device through the antenna section, and/or to receive data, sent from the external device and to be fed into the information processing section, in order to implement a wireless communication with the external device.

(2) According to another aspect of the present invention, in the information processing apparatus recited in item 1, the wearing section is formed in a closed annulus shape.

(3) According to still another aspect of the present invention, in the information processing apparatus recited in item 1, the wearing section is formed in any one of a one-side open rectangular shape, a character "C" shape and a character "U" shape.

(4) According to still another aspect of the present invention, the information processing apparatus recited in item 1, further comprises: a sensor to detect living body information in regard to the living body or environmental information in regard to a peripheral space; wherein both the living body information and the environmental information, detected by the sensor, are processed in the information processing section, so as to transmit processed data to the external device through the communication section and the antenna section.

(5) According to still another aspect of the present invention, in the information processing apparatus recited in item 1, data transmitting operations are conducted between the information processing apparatus and another information processing apparatus, both of which are worn on the same living body.

(6) According to yet another aspect of the present invention, in the information processing apparatus recited in item 1, the information processing apparatus is incorporated into any one of a wrist watch, a head mount display, a headphone, a digital camera and various kinds of portable terminal devices.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

BEST MODE FOR IMPLEMENTING THE INVENTION

Figure 1:
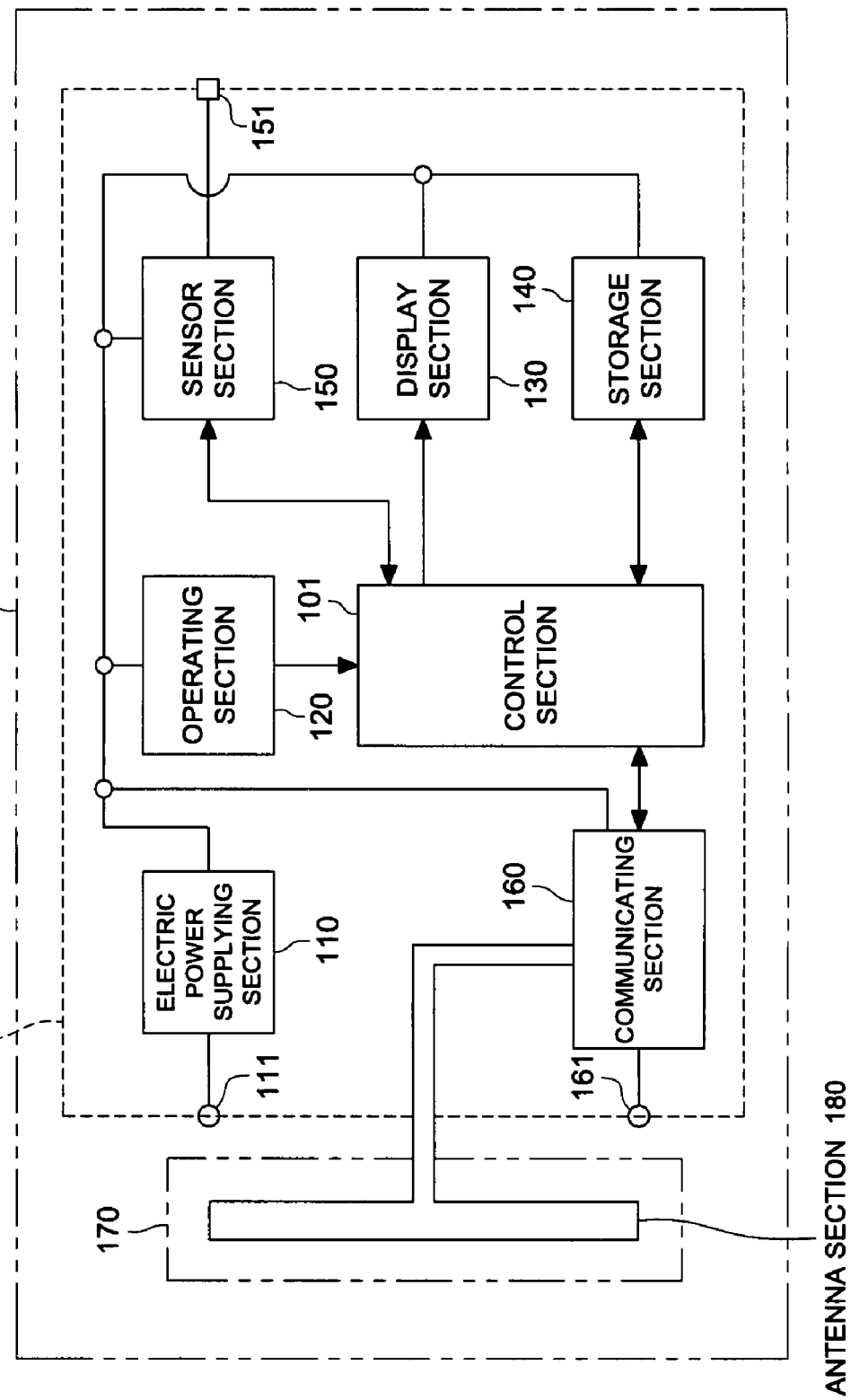
FIG. 1 shows a block diagram indicating a brief configuration of information processing apparatus 100 embodied in the present invention.

Referring to the drawings, the best mode for implementing the invention will be detailed in the following.

Namely, preferable embodiments of information processing apparatus as the best mode for implementing the present invention will be detailed in the following. However, the scope of the present invention is not limited to the embodiments described in the following.

First Embodiment

Overall Configuration

An information processing apparatus 100, shown in FIG. 1, is fitted on a living body as a wearable device in such a manner that a wearing section 170 provided with an antenna section 180 surrounds a part of the living body. In this state, processed data processed in an information processing section are transmitted to external apparatuses from the antenna section 180, while received data received from the external apparatuses through the antenna section 180 are inputted into the information processing section. Namely, the information processing apparatus 100 has a function for implementing wireless communications with the external apparatuses. Wherein, the external apparatuses include other wearable devices and stationary devices.

Incidentally, the wearable device is defined as such a device that is wearable on a living body, such as a human body, etc., and not only is an exclusively designed device, but also includes such a device that is incorporated into any one of a wrist watch, a head mount display, a headphone, a digital camera, various kinds of portable terminal devices, etc.

Now, as shown in FIG. 1, the information processing apparatus 100, serving as a wearable device, includes a control section 101, an electric power supplying section 110, an operating section 120, a display section 130, a storage section 140, a sensor section 150, a communicating section 160, the wearing section 170 and the antenna section 180, as main structural elements. Other than the above, the information processing apparatus 100 further includes an external power supply terminal 111, a sensor detecting section 151 and a communication terminal 161.

The control section 101 is constituted by a CPU (Central Processing Unit), a ROM (Read Only Memory), etc., which are not shown in the drawings, so as to implement various kinds of controlling and processing operations based on programs stored in the ROM. Further, the control section 101 also serves as the information processing section to conduct the wireless communications between the information processing apparatus 100 and other devices (namely, the external devices).

The electric power supplying section 110 is constituted by a buttery or a rechargeable buttery, a boost up circuit and a constant voltage circuit, so as to supply electric power to each of the sections included in the information processing apparatus 100. Incidentally, the electric power supplying section 110 conducts a recharging operation by employing electric power fed from an external power supply through the external power supply terminal 111 provided on the casing surface of the information processing apparatus 100.

The operating section 120 is constituted by various kinds of functional buttons, various kinds of knobs, various kinds of icons indicated on the display section 130 detailed later, etc., so as to output operating signals, corresponding to the operator's inputting actions, to the control section 101. Alternatively, the control section 101 reads the operator's inputting actions conducted on the operating section 120.

The display section 130 is constituted by a flat panel display, such as a LCD display (Liquid Crystal Display), an organic EL (Electro Luminescence), etc., so as to display various kinds of statuses, various kinds of operating screens for assisting the operator's inputting actions conducted on the operating section 120 as mentioned in the above, etc., in response to the instructions outputted from the control section 101.

The storage section 140 is constituted by volatile storages, such as SRAMs (Static Random Access Memory), SDRAMs (synchronous Dynamic Random Access Memory), etc., and/or nonvolatile storages, such as FLASHROMs, EPROMs, FRAMs, etc. Incidentally, the storage section 140 stores various kinds of setting data of the information processing apparatus 100, various kinds of data pertaining to the information processing, etc.

The sensor section 150, serving as a detector for detecting living body information in regard to the living body, which wears the information processing apparatus 100, or for detecting environmental information in regard to the peripheral space, is provided with a sensor detecting section 151. Both the living body information and the environmental information, detected by the sensor section 150, are processed in an information processing section (namely, control section 101), so as to transmit the processed data to external devices through a communication section and an antenna section detailed later.

The communicating section 160 conducts a wireless communication in such a manner that the communicating section 160 transmits the data processed by the information processing section (namely, control section 101) to the external devices through the antenna section detailed later, while supplies data received from the external devices through the antenna section to the information processing section (namely, control section 101).

Further, the communicating section 160 also conducts a wired communication in such a manner that the communicating section 160 transmits the data processed by the information processing section (namely, control section 101) to the external devices through a communication line coupled to the communication terminal 161, while supplies data received from the external devices through the communication line, coupled to the communication terminal 161, to the information processing section (namely, control section 101).

Incidentally, it is applicable that the communication terminal 161 and the external power supply terminal 111 are integrally configured, or both the wired communication and the external power supply are achieved through the same connection cable or the same cradle.

The antenna section 180 formed as a loop antenna or a dipole antenna embedded into a wearing section detailed later, and serves as a transmitting antenna, a receiving antenna or a transmit-receive antenna for conducting the wireless communication between the communicating section 160 and the external device. Incidentally, it is preferable that the antenna section 180 is configured so as to tune with a frequency of an electro-magnetic wave to be employed for the wireless communication.

The wearing section 170 serves as a wearable material, such as various kinds of belts, eyeglasses, a frame of head mount display, a head band, a neck band, a wrist band, a hand strap, a neck strap, a ring, etc., which makes it possible to wear the information processing apparatus 100 on the living body by surrounding a part of the living body (human body). Further, the antenna section 180 is formed on the surface of or inside the wearing section 170, or the wearing section 170 itself is formed as the antenna section 180.

Figure 2:
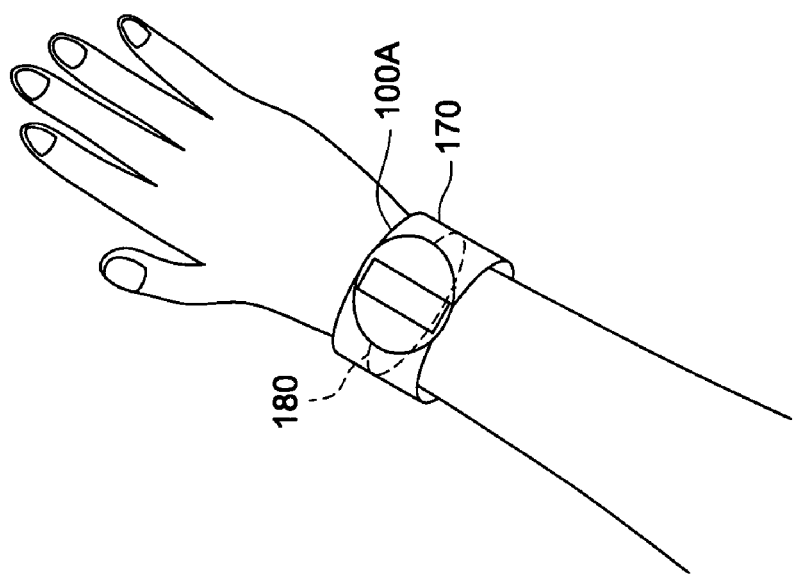
FIG. 2(a), FIG. 2(b) and FIG. 2(c) show explanatory schematic diagrams indicating outer appearances of applied examples of information processing apparatus 100 embodied in the present invention.
Figure 2:
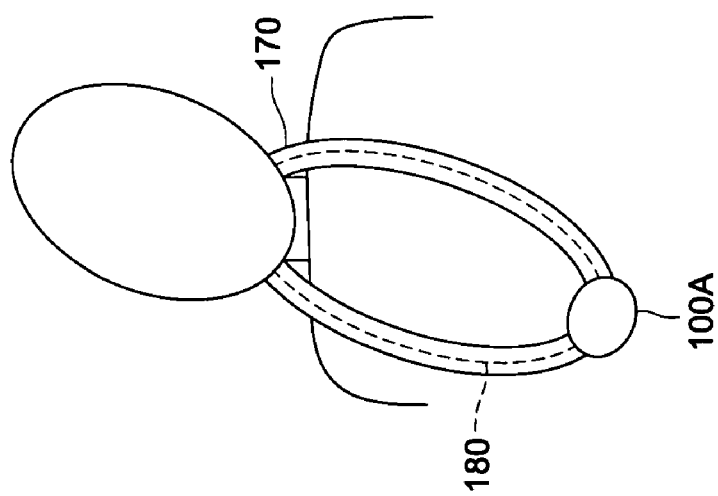
Figure 2:
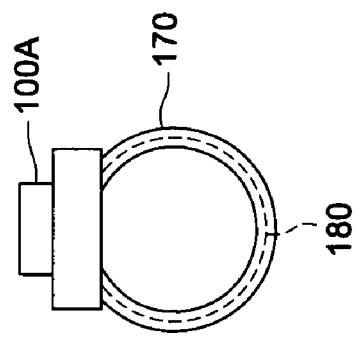

For instance, when the information processing apparatus 100 is applied to the ring as shown in FIG. 2(*a*), a main section 100A of the information processing apparatus 100 (namely, a part from which the wearing section 170 and the antenna section 180 are excluded) is mounted on a pedestal area of the ring, and a portion "c" of the ring is used as the wearing section 170. Incidentally, if the annular portion of the ring is made of metal, it can be employed for the antenna section 180 as it is.

Further, when the information processing apparatus 100 is applied to the necklace or the neck strap as shown in FIG. 2(*b*), the main section 100A of the information processing apparatus 100 (namely, a part from which the wearing section 170 and the antenna section 180 are excluded) is mounted on the wearing section 170 of the necklace, the neck strap, etc., and the antenna section 180 is disposed inside or on the surface of the necklace or the neck strap.

Still further, when the information processing apparatus 100 is applied to the wristwatch as shown in FIG. 2(*c*), the main section 100A of the information processing apparatus 100 (namely, a part from which the wearing section 170 and the antenna section 180 are excluded) is mounted on the wearing section 170, such as a watch belt, etc., and the antenna section 180 is disposed inside or on the surface of the watch belt.

Incidentally, it is applicable that the wearing section 170 is formed in not only such the closed annular shape as shown in the above, but also in an open annular shape, such as a one-side open rectangular shape, a character "C" shape or a character "U" shape.

Further, it is applicable that any one of the same or the same kind of wearable apparatus, various kinds of apparatuses and devices, which is capable of communicating with the information processing apparatus 100, is employed as the external device (not shown in the drawings) mentioned in the above.

Figure 3:
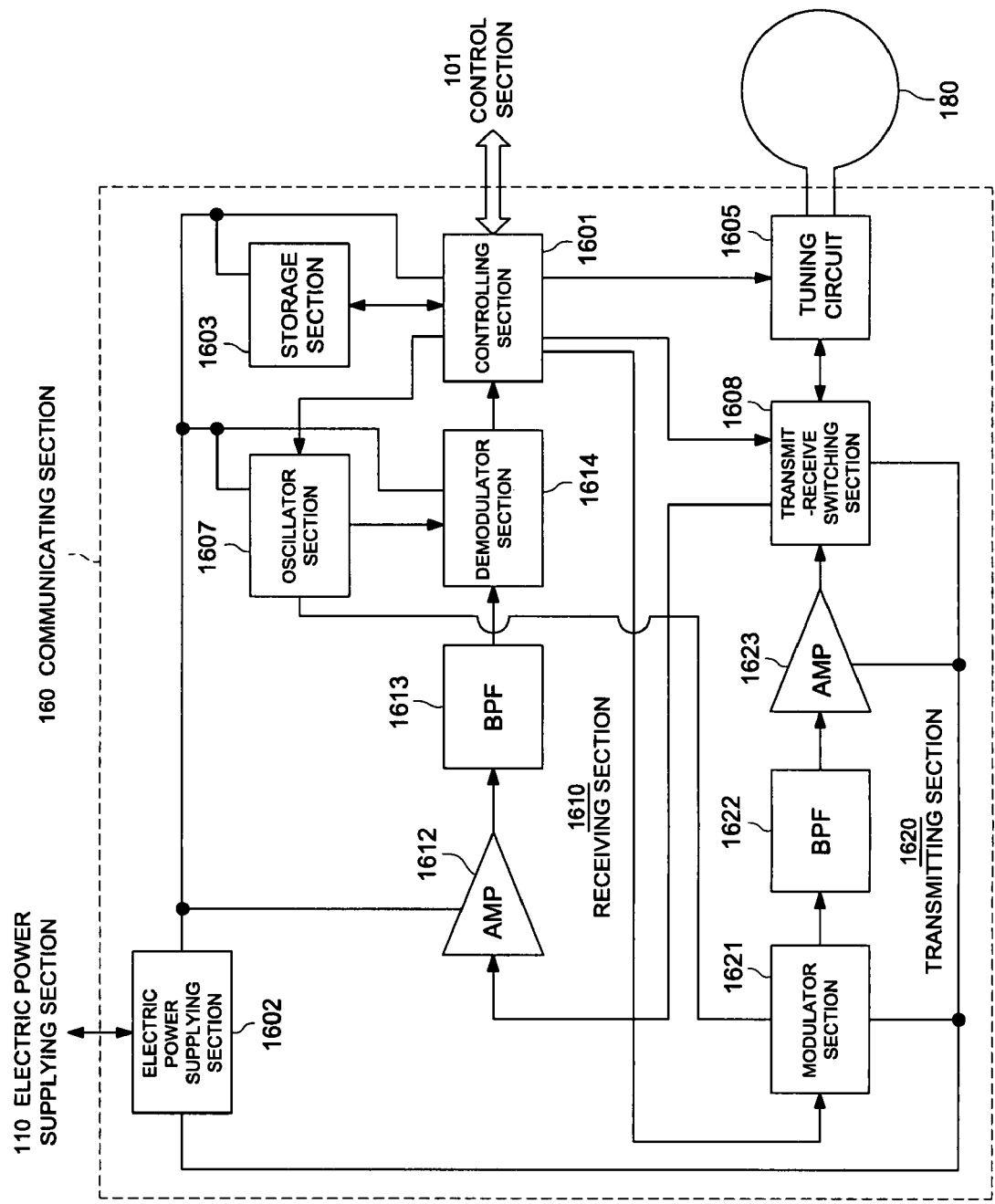
FIG. 3 shows a block diagram indicating a brief configuration of communicating section 160 serving as a main section of the information processing apparatus 100 embodied in the present invention.

Now, referring to FIG. 3, the configuration of the communicating section 160 in the information processing apparatus 100 will be detailed in the following. Hereinafter, the communicating section 160 provided with a receiving section 1610 and a transmitting section 1620 will be detailed.

A controlling section 1601 is constituted by a CPU (Central Processing Unit), a ROM (Read Only Memory), etc., so as to implement various kinds of controlling operations and various kinds of processing in regard to the transmitting and receiving operations, based on various kinds of programs stored in the ROM. Incidentally, it is applicable that the apparatus is so constituted that the control section 101 of the information processing apparatus 100 also serves as the controlling section 1601.

An electric power supplying section 1602 is constituted by a battery or a rechargeable battery, a voltage boost-up circuit and a constant voltage circuit, so as to supply electric power to each of the sections included in the information processing apparatus 100. Incidentally, it is applicable that the apparatus is so constituted that the electric power supplying section 110 of the information processing apparatus 100 also serves as the electric power supplying section 1602.

A storage section 1603 is constituted by volatile memories, such as a SRAM (Static Random Access Memory), a SDRAM (Synchronous Dynamic Random Access Memory), etc., or nonvolatile memories, such as a FLASHROM, an EEPROM, a FRAM, etc., so as to store various kinds of setting data of the communicating section 160, various kinds of data in respect to the transmit-receive operations and the information processing operations. Incidentally, it is applicable that the apparatus is so constituted that the storage section 140 of the information processing apparatus 100 also serves as the storage section 1603.

A tuning circuit 1605 is constituted by a resonance circuit, an impedance matching circuit, etc., so as to serve as a kind of filter in tune with the frequency of the electro-magnetic waves employed for the transmit-receive operations. In addition, the tuning circuit 1605 has a function of matching the impedance of the antenna section 180 disposed in such a manner that it surrounds a part of the living body.

In response to the controlling actions of the controlling section 1601, an oscillator section 1607 generates carrier wave signals to be employed in the transmitting section, and local oscillation signals to be employed for the frequency conversion processing conducted in the receiving section and for the demodulating operation.

When the antenna section 180 is used for both transmitting and receiving operations, a transmit-receive switching section 1608 switches the operating mode of the antenna section 180 between the transmitting mode and the receiving mode.

Numeral 1610 indicates the receiving section to receive the electro-magnetic wave transmitted from the other apparatus (namely, the external apparatus) through the antenna section 180, and is constituted by a reception amplifier 1612 to conduct a high-frequency signal amplifying operation, a band pass filter 1613 to conduct a frequency band limiting operation, a center frequency of which is set at the frequency of the received signals and a demodulator section 1614 to demodulate the received signals according to the predetermined detection method so as to extract data. The data extracted by the demodulator section 1614 (received image data) are fed into the controlling section 1601.

Numeral 1620 indicates the transmitting section to transmit the electro-magnetic wave to the other apparatus (namely, the external apparatus) through the antenna section 180, and is constituted by a modulator section 1621 to modulate the carrier wave signals with data to be transmitted (namely, the transmission data outputted from the controlling section 1601) according to the predetermined modulation method, a band pass filter 1622 to conduct a frequency band limiting operation, a center frequency of which is set at the frequency of the transmission signals and a transmission amplifier 1623 to conduct a high-frequency signal power amplifying operation. The radio-frequency transmission signals, generated by modulating the carrier wave signals with the transmission data outputted from the controlling section 1601, are power-amplified, so as to transmit the radio-frequency transmission signals from the antenna section 180 to the external device.

Figure 4:
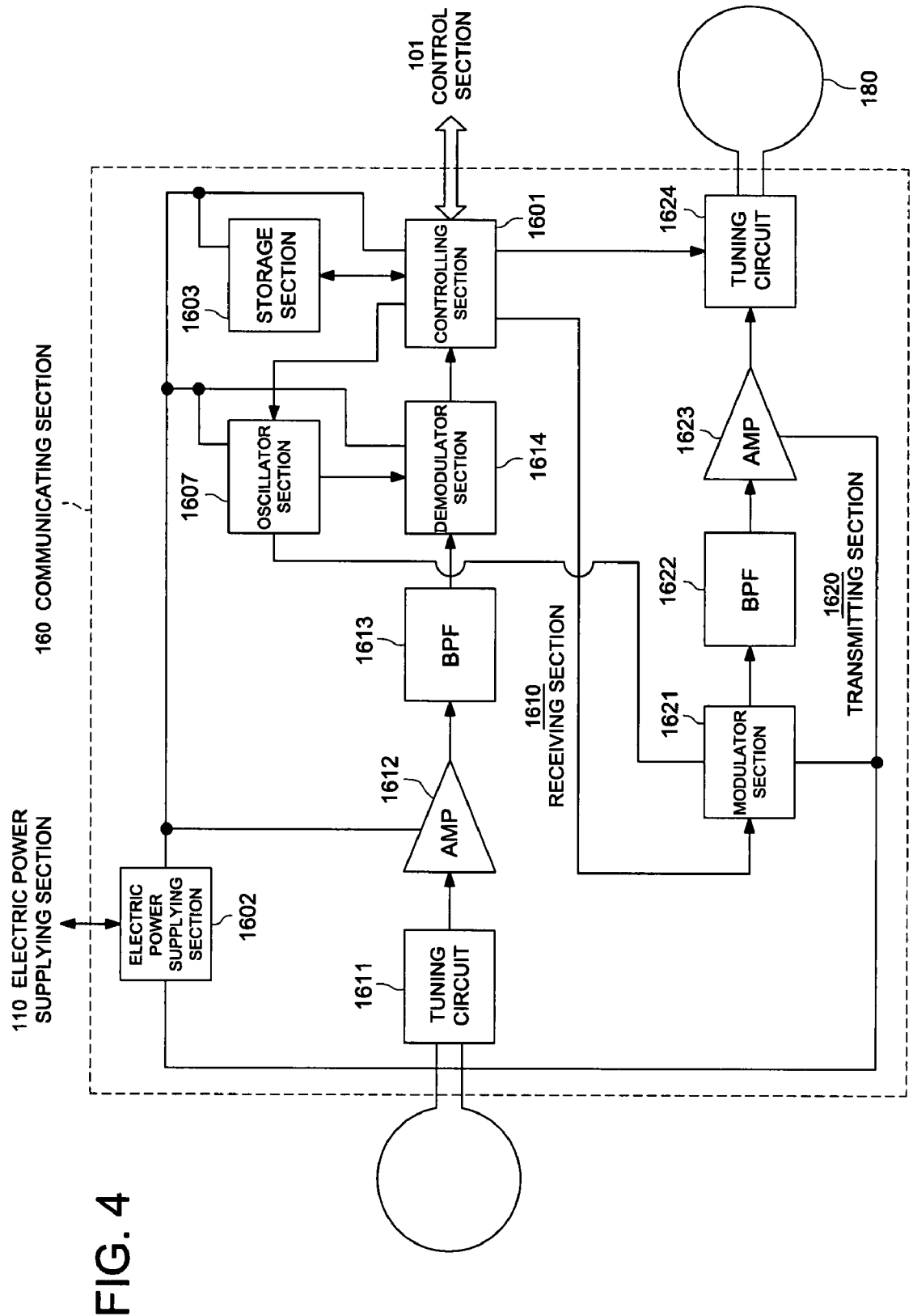
FIG. 4 shows a block diagram indicating another example of brief configuration of communicating section 160 serving as a main section of the information processing apparatus 100 embodied in the present invention.

Incidentally, as shown in FIG. 4, it is also possible to divide the antenna section 180 into a reception antenna 180a and a transmission antenna 180b. In this configuration, the reception antenna 180a is coupled to a tuning circuit 1611 of the receiving section 1610, and the reception processing thereafter are the same as those shown in FIG. 3. Further, in this configuration, the transmission antenna 180b is coupled to a tuning circuit 1624 of the transmitting section 1620, and the transmission processing therebefore are the same as those shown in FIG. 3. Still further, in this configuration, the transmit-receive switching section can be eliminated.

Further, it is also possible that the receiving section 1610 and the transmitting section 1620 are provided as the separate circuits, each of which is provided with an independent controlling section and an independent storage section, in the communicating section 160. Still further, it is also possible that any one of the receiving section 1610 and the transmitting section 1620 is employed as the necessary circuit in the communicating section 160.

<Operations>

Figure 5:
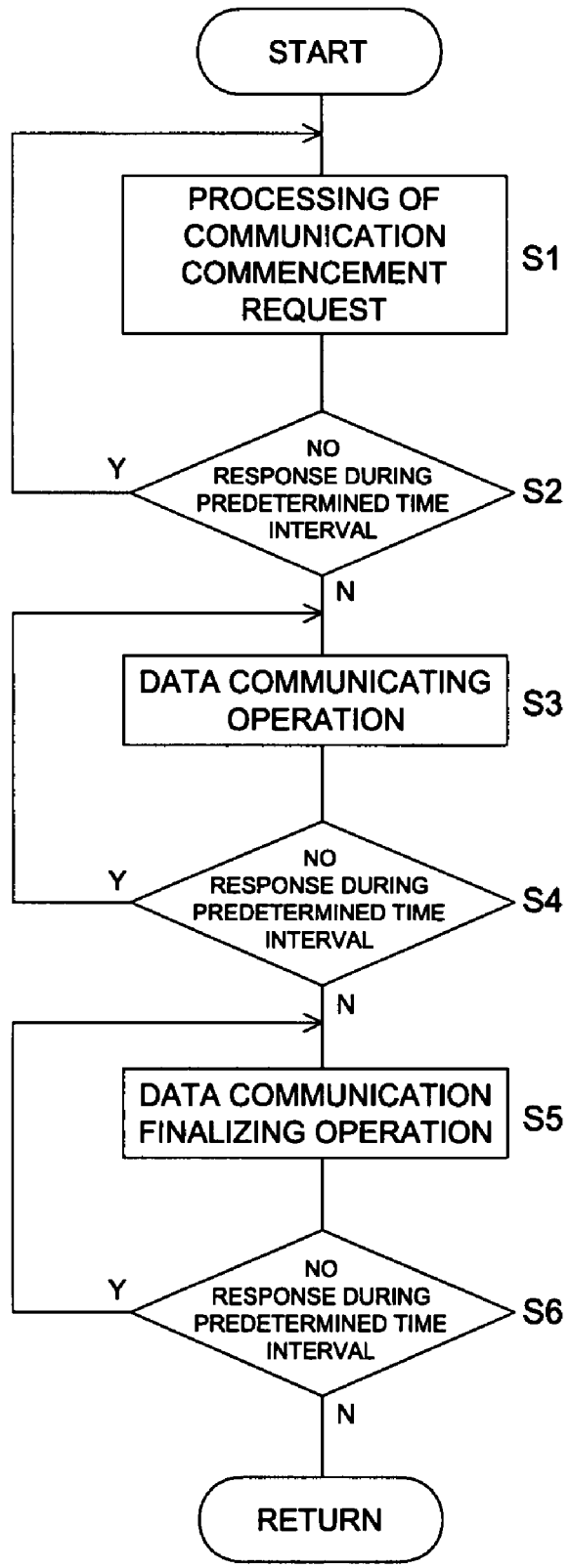
FIG. 5 shows a flowchart indicating operating statuses of information processing apparatus 100 embodied in the present invention.

Referring to the flowchart shown in FIG. 5, the operations of the information processing apparatus 100 will be detailed in the following. FIG. 5 shows controlling statuses of the control section 101 when the information processing apparatus 100 conducts the wireless communication with the other apparatus (namely, the external devices). Hereinafter, the external devices with which the information processing apparatus 100 conducts the wireless communication are the other wearable apparatus having the communicating function and another stationary apparatus having the communicating function.

The control section 101 operates according to the operating program for the wearable apparatus, and monitors inputting operations on the operating section 120 conducted by the user and the detecting results of the sensor section 150. Then, at the time when the communication with the external device becomes necessary, the control section 101 tries to establish the communication with the external device according to the flowchart shown in FIG. 5.

Comment: According to the state transition diagrams detailed later, in each operation of the communication commencement request, the data communication processing and the communication completion processing, when no response is received, the concerned signal is retransmitted in each of the abovementioned operations. Accordingly, in order to avoid contradictions with those state transition diagrams, the returning destination in the flowchart shown in FIG. 5 when no response is received is changed.

Now, precedent to the commencement of the communication with the external device, the control section 101 transmits a command signal for requesting the commencement of the communication, which is modulated on the carrier wave having the predetermined frequency, to the external device from the antenna section 180 as the radio-wave transmission signals (Step S1 shown in FIG. 5). In this connection, the control section 101 waits in a standby mode while the communicating section 160 enters in the receiving mode for receiving radio-wave signals caught by the antenna section 180, so as to determine whether or not radio-wave response signals modulated with an acknowledgement response (ACK), which indicates that the request of the commencement of the communication is accepted, are sent back from the external device, during a predetermined time interval since the command signal (ENQ) for requesting the commencement of the communication was transmitted to the external device (Step S2 shown in FIG. 5).

When the control section 101 cannot confirm that the radio-wave response signals modulated with the acknowledgement response (ACK), which indicates that the request of the commencement of the communication is accepted, are sent back from the external device, and receives by the communicating section 160 (Step S2; Yes, shown in FIG. 5) during the predetermined time interval mentioned in the above, the control section 101 again transmits the radio-wave response signals, modulated with the command signal (ENQ) for requesting the commencement of the communication precedent to the commencement of the communication with the external device, to the external device through the antenna section 180 (Step S1, shown in FIG. 5).

If the control section 101, serving as an information processing section, can confirm that the radio-wave response signals modulated with the acknowledgement response (ACK), which indicates that the request of the commencement of the communication is accepted, are sent back from the external device, and receives by the communicating section 160 (Step S2; No, shown in FIG. 5) during the predetermined time interval mentioned in the above, the control section 101 commences the data communication with the external device according to the predetermined communication procedure (Step S3, shown in FIG. 5). In this connection, the control section 101 continues the data communicating operation with the external device, until all of the necessary data transactions to be conducted between the information processing apparatus 100 and the external device have been completed.

Further, during the abovementioned data communicating operation (Step S3, shown in FIG. 5), when the control section 101, serving as an information processing section, confirms that an absence status of the response to be sent from the external device continues longer than the predetermined time interval (Step S4; Yes, shown in FIG. 5), the control section 101 determines that the communication operating state can be no longer maintained, and again commences the data communicating operation with the external device according to the predetermined communication procedure (Step S3, shown in FIG. 5).

Then, at the time when all of the necessary data transactions to be conducted between the information processing apparatus 100 and the external device have been completed, the control section 101, serving as an information processing section, implements the data communication finalizing operation so as to finalize the processing of the routine (Step S5, shown in FIG. 5).

Further, during the data communication finalizing operation mentioned in the above (Step S5, shown in FIG. 5), when the control section 101, serving as an information processing section, confirms that an absence status of the response to be sent from the external device continues longer than the predetermined time interval (Step S6; Yes, shown in FIG. 5), the control section 101 determines that the communication operating state can be no longer maintained, and again commences the data communicating operation with the external device according to the predetermined communication procedure (Step S5, shown in FIG. 5).

In each of steps included in the aforementioned flowchart, the information processing apparatus 100, serving as the wearable apparatus, is worn on the living body by making the wearing section 170 surround a part of the living body. Further, since the wireless communication is achieved through the antenna section 180, configured as a dipole antenna or a loop antenna, and formed (or embedded) in the wearing section 170, it becomes possible to avoid a direct contact between the electrode and the surface of the living body when wearing it. Further, since the radio-wave signals propagate around the surface of the living body in the vicinity of the wearing section 170 worn on the living body, it becomes possible not only to reduce the divergence of the data towards the peripheral space, but also to conduct the communication, which is superior in the transmission efficiency.

Further, since the radio-wave signals propagate around the surface of the living body in the vicinity of the wearing section 170 worn on the living body to conduct the wireless communication, a little amount of the radio-wave signals modulated by the data diverges around the peripheral space, and accordingly, it becomes possible to conduct communicating operations, which consume a relatively small amount of electric power, compared to that consumed in the conventional apparatus. Therefore, it becomes possible to obtain an effect of reducing the power dissipation of the information processing apparatus 100.

Further, even when a range of the strength of the electric field or a range of the transmission radio-wave power is specified by a certain radio-wave regulation concerning to the feeble electric wave communication or the specified low power communication, such as Wireless Telegraphy Act, or the like, since the wireless communication is performed in such a manner that the radio-wave signals propagate around the surface of the living body in the vicinity of the wearing section 170 worn on the living body, it becomes possible to conduct secure communicating operations consuming a small amount of electric power lower than that in the conventional apparatus, resulting in improvement of its reliability.

Next, with respect to the request of the commencement of the communication aforementioned (Step S1, shown in FIG. 5), detailed explanations will be given in the following, referring to the state transition diagram shown in FIG. 6.

Figure 6:
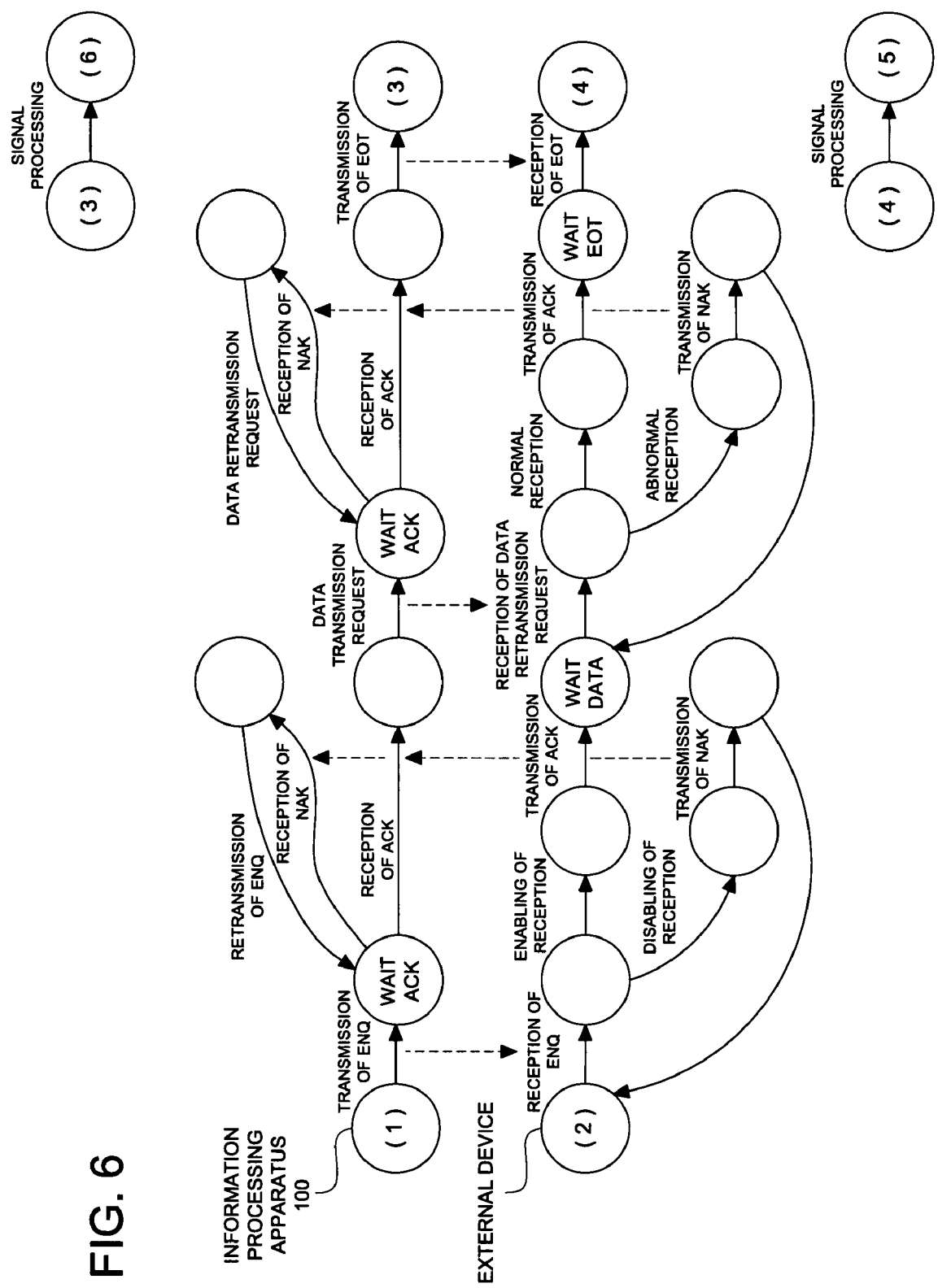
FIG. 6 shows a state transition diagram indicating operating statuses at the time of a communication commencement request of information processing apparatus 100 embodied in the present invention.

At first, the control section 101 of the information processing apparatus 100 commences the processing of the request of the commencement of the communication from the initial phase (1) shown in FIG. 6. Then, the control section 101 waits an arrival of the acknowledgement response (waiting the ACK response), which indicates that the request of the commencement of the communication is accepted, and which is to be sent back from the external device, during the predetermined time interval since the control section 101 has sent the command signal of the communication commencement request (transmitting the ENQ command, namely, transmission control character "ENQUIRY").

On the other hand, when the external device (not shown in the drawings) cannot receive the radio-wave signals modulated by the command signal of the communication commencement request sent from the information processing apparatus 100 (disable of receiving the ENQ command), or cannot correctly demodulate the command signal of the communication commencement request from the received radio-wave signals, the controlling section (not shown in the drawings) of the external device determines that it is impossible to receive the ENQ command. Then, the controlling section sends the radio-wave signals modulated with the NAK response (NEGATIVE ACKNOWLEDGE, being a transmission control character transmitted by a receiver as a negative response to the sender, representing that the data are not correctly received) and having a predetermined frequency to the information processing apparatus 100 (transmission of the NAK response).

In this connection, when the command signal acquired by demodulating the radio-wave signals sent from the external device through the antenna section 180 is the NAK response (being the negative response representing that the data are not correctly received), the control section 101 controls the communicating section 160 so as to retransmit the radio-wave signals modulated with the command signal of the communication commencement request and having a predetermined frequency through the antenna section 180 (retransmission of the ENQ command).

Further, when the external device can receive the radio-wave signals sent from the information processing apparatus 100 and can demodulate the command signal of the communication commencement request (enable of receiving the ENQ command), the controlling section of the external device (not shown in the drawings) determines that the ENQ command is correctly received. Then, at the time when the preparing operations to be conducted at the external device side are completed, the controlling section of the external device transmits the radio-wave signals modulated with the ACK response (ACKNOWLEDGE, being a transmission control character transmitted by a receiver as an affirmative response to the sender, representing that all of the transmitted data are correctly received and the preparation for receiving the next data is completed) to the information processing apparatus 100 (transmission of the ACK response).

At this time, if the control section 101 of the information processing apparatus 100 can receives the radio-wave signals sent from the external device and can demodulate the ACK response (enable of receiving the ACK response), the control section 101 determines that the communication with the external device is established and the preparation at the external device side is already completed, and then, transmits the radio-wave signals modulated with a command signal for requesting data to the external device (transmission of the data requesting command).

In this connection, when the external device cannot receive the radio-wave signals modulated by the command signal for requesting data sent from the information processing apparatus 100 (disable of receiving the data requesting command), or cannot correctly demodulate the command signal for requesting data from the received radio-wave signals, the controlling section of the external device determines that the current reception is abnormal. Then, the controlling section sends the radio-wave signals modulated with the NAK response (being the negative response representing that the data are not correctly received) and having a predetermined frequency to the information processing apparatus 100 (transmission of the NAK response).

At this time, if the command signal acquired by demodulating the radio-wave signals sent from the external device through the antenna section 180 is the NAK response (being the negative response representing that the data are not correctly received), the control section 101 controls the communicating section 160 so as to retransmit the radio-wave signals modulated with the command signal for requesting data and having the predetermined frequency-through the antenna section 180 (retransmission of the data requesting command).

Further, when the external device can receive the radio-wave signals sent from the information processing apparatus 100 and can demodulate the command signal for requesting data (enable of receiving the data requesting command), the controlling section of the external device determines that the command signal for requesting data is correctly received. Then, at the time when the preparing operations to be conducted at the external device side are completed, the controlling section of the external device transmits the radio-wave signals modulated with the ACK response (being a transmission control character transmitted by a receiver as an affirmative response to the sender, representing that all of the transmitted data are correctly received and the preparation for receiving the next data is completed) to the information processing apparatus 100 (transmission of the ACK response).

At this time, if the control section 101 of the information processing apparatus 100 can receives the radio-wave signals sent from the external device and can demodulate the ACK response (enable of receiving the ACK response), the control section 101 determines that the communication with the external device in respect to the request of data is established and the preparation in respect to the request of data at the external device side is already completed. Then, the control section 101 transmits the radio-wave signals modulated with the EOT (END OF TRANSMISSION) command, being a transmission control character or bits used to indicate the conclusion of the processing concerning to this communication commencement request, to the external device (transmission of the EOT), so as to finalize the processing for this communication commencement request (phase (3) shown in FIG. 6).

On the other hand, when the external device can receive the radio-wave signals sent from the information processing apparatus 100 and can demodulate the EOT command (enable of receiving the EOT command), the controlling section of the external device determines that the processing for the request of commencing the communication with the information processing apparatus 100 is completed, and finalizes the processing for this communication commencement request (phase (4) shown in FIG. 6).

Next, with respect to the aforementioned data communicating operation (Step S3, shown in FIG. 5), detailed explanations will be given in the following, referring to the state transition diagram shown in FIG. 7.

Figure 7:
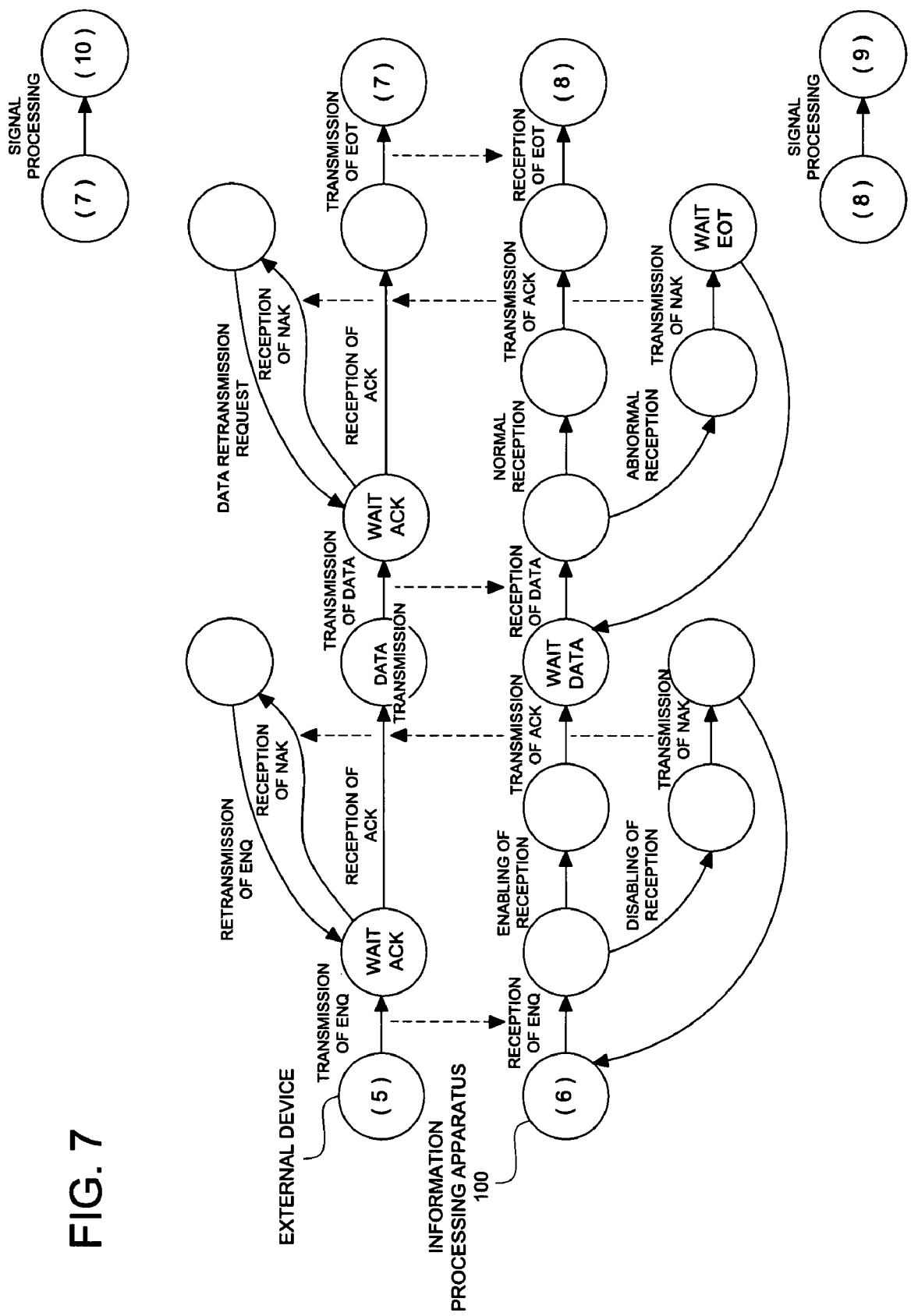
FIG. 7 shows a state transition diagram indicating operating statuses at the time of data communication of information processing apparatus 100 embodied in the present invention.

At first, the external device, which finalizes the aforementioned processing for the communication commencement request (phase (4) shown in FIG. 6), commences the processing of the abovementioned data communicating operation from the initial phase (5) shown in FIG. 7, and at this time, transmits the radio-wave signals, modulated with the ENQ command and having a predetermined frequency, to the information processing apparatus 100, in order to confirm whether or not the information processing apparatus 100, serving as a reception terminal device, completes the preparation for receiving the next data (transmission of the ENQ command). Then, the external device waits an arrival of the ACK response indicating the completion of the preparation and to be sent back from the information processing apparatus 100, during the predetermined time interval since the external device has sent the ENQ command (waiting the ACK response).

On the other hand, the information processing apparatus 100, which finalizes the aforementioned processing for the communication commencement request (phase (3) shown in FIG. 6), commences the processing of the abovementioned data communicating operation from the initial phase (6) shown in FIG. 7. When the information processing apparatus 100 cannot receive the radio-wave signals modulated by the ENQ command sent from the external device (disable of receiving the ENQ command), or cannot correctly demodulate the ENQ command from the received radio-wave signals, the information processing apparatus 100 determines that it is impossible to receive the ENQ command. Then, the information processing apparatus 100 sends the radio-wave signals, modulated with the NAK response (being the negative response representing that the data are not correctly received) and having a predetermined frequency, to the external device (transmission of the NAK response).

In this connection, when the command signal acquired by demodulating the radio-wave signals received from the information processing apparatus 100 is the NAK response (being the negative response representing that the data are not correctly received), the external device retransmits the radio-wave signals, modulated with the ENQ command and having the predetermined frequency, (retransmission of the ENQ command).

Further, when the information processing apparatus 100 can receive the radio-wave signals sent from the external device and can demodulate the ENQ command (enable of receiving the ENQ command), the control section 101 of the information processing apparatus 100 determines that the ENQ command is correctly received. Then, at the time when the preparing operations to be conducted at the information processing apparatus 100 side are completed, the control section 101 of the information processing apparatus 100 transmits the radio-wave signals modulated with the ACK response (being the transmission control character transmitted by the receiver as the affirmative response to the sender, representing that all of the transmitted data are correctly received and the preparation for receiving the next data is completed) to the external device (transmission of the ACK response). Then, the control section 101 of the information processing apparatus 100 waits arrival of the data sent from the external device associating with the commencement of the data communication at the external device side (waiting data).

At this time, if the external device can receives the radio-wave signals sent from the information processing apparatus 100 and can demodulate the ACK response (enable of receiving the ACK response), the external device determines that the communication with the information processing apparatus 100 is established and the preparation at the information processing apparatus 100 side is already completed, and then, commences the data communicating operations (transmission of the data). Concretely speaking, the external device transmits the radio-wave signals, modulated with the data and having the predetermined frequency, to the information processing apparatus 100.

In this connection, when the information processing apparatus 100 cannot receive the radio-wave signals modulated with the data sent from the external device (disable of receiving the data), or cannot correctly demodulate the data from the received radio-wave signals, the control section 101 of the information processing apparatus 100 determines that the current reception is abnormal. Then, the control section 101 sends the radio-wave signals, modulated with the NAK response (being the negative response representing that the data are not correctly received) and having a predetermined frequency, to the external device (transmission of the NAK response).

On the other hand, the external device waits an arrival of the ACK response to be sent from the information processing apparatus 100, after transmitting the predetermined data according to the data communicating operations. When the command signal acquired by demodulating the radio-wave signals received from the information processing apparatus 100 is the NAK response (being the negative response representing that the data are not correctly received), the external device retransmits the radio-wave signals, modulated with the data concerned and having the predetermined frequency, to the information processing apparatus 100 (retransmission of the data).

Further, at this time, if the external device can receives the radio-wave signals sent from the information processing apparatus 100 and can demodulate the ACK response (enable of receiving the ACK response), the controlling section of the external device determines that the communication with the information processing apparatus 100, in respect to the data communication, is already completed. Then, the external device transmits the radio-wave signals modulated with the EOT (END OF TRANSMISSION) command, being a transmission control character or bits used to indicate the conclusion of the processing concerning to this data communication, to the information processing apparatus 100 (transmission of the EOT), so as to finalize the processing for this data communication (phase (7) shown in FIG. 7).

On the other hand, when the information processing apparatus 100 can receive the radio-wave signals sent from the external device and can demodulate the EOT command (enable of receiving the EOT command), the control section 101 of the information processing apparatus 100 determines that the processing for the data communication with the external device is completed, and finalizes the processing for this data communication (phase (8) shown in FIG. 7).

Next, with respect to the aforementioned data communication finalizing processing (Step S5, shown in FIG. 5), detailed explanations will be given in the following, referring to the state transition diagram shown in FIG. 8.

Figure 8:
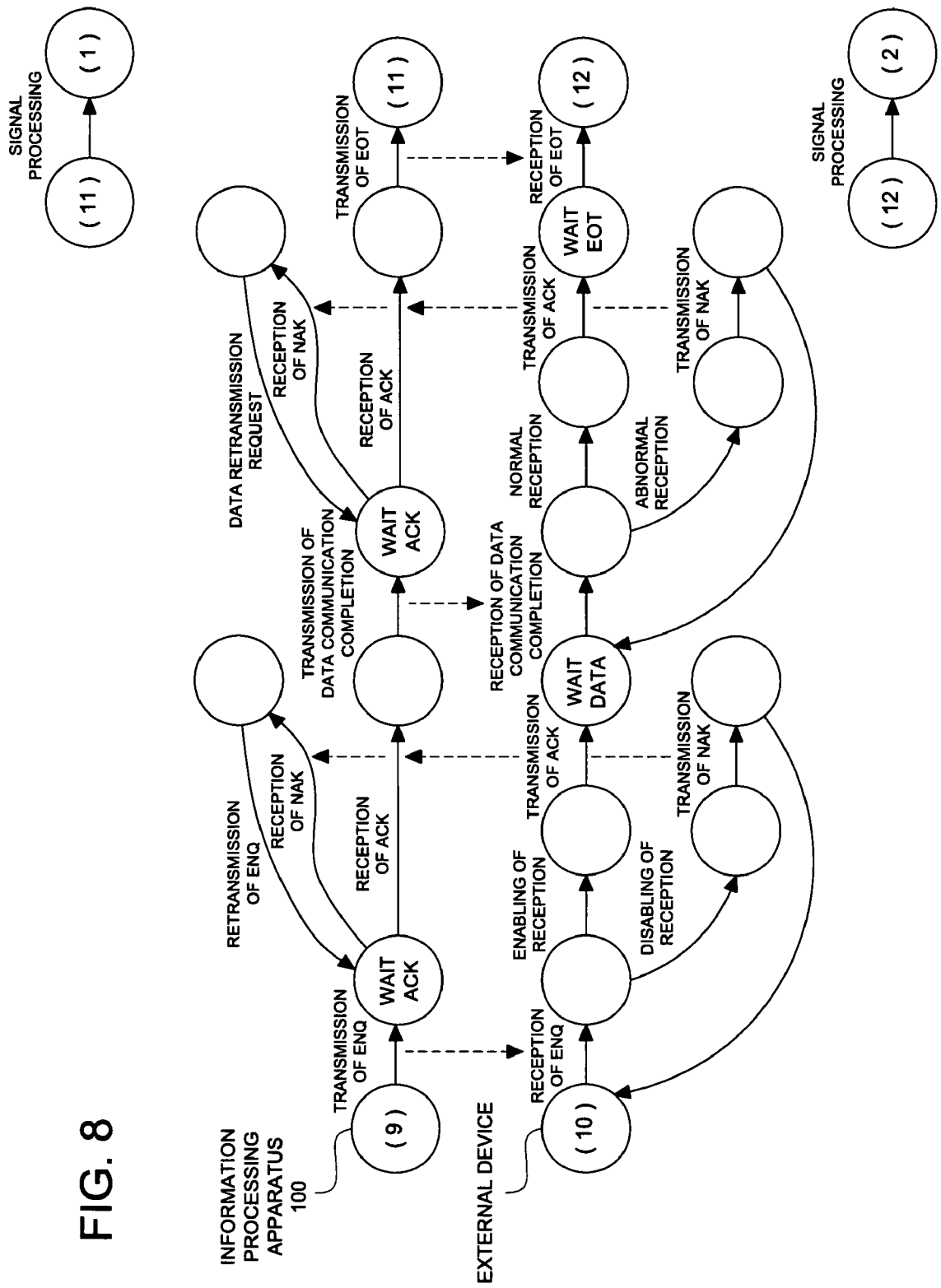
FIG. 8 shows a state transition diagram indicating operating statuses at the time when completing the data communication of information processing apparatus 100 embodied in the present invention.

At first, the information processing apparatus 100, which finalizes the aforementioned processing for the data communication (phase (8) shown in FIG. 7), commences the data communication finalizing processing from the initial phase (9) shown in FIG. 8, and at this time, transmits the radio-wave signals, modulated with the ENQ command and having a predetermined frequency, to the external device, in order to confirm whether or not the external device, serving as a reception terminal device, completes the preparation for receiving the next command signal and the next data (transmission of the ENQ command). Then, the information processing apparatus 100 waits an arrival of the ACK response indicating the completion of the preparation and to be sent back from the external device, during the predetermined time interval since the information processing apparatus 100 has sent the ENQ command (waiting the ACK response).

On the other hand, the external device, which finalizes the aforementioned processing for the communication commencement request (phase (7) shown in FIG. 7), commences the processing of the abovementioned data communicating operation from the initial phase (10) shown in FIG. 8. When the external device cannot receive the radio-wave signals modulated by the ENQ command sent from the information processing apparatus 100 (disable of receiving the ENQ command), or cannot correctly demodulate the ENQ command from the received radio-wave signals, the external device determines that it is impossible to receive the ENQ command. Then, the external device sends the radio-wave signals, modulated with the NAK response (being the negative response representing that the data are not correctly received) and having a predetermined frequency, to the information processing apparatus 100 through its antenna section (transmission of the NAK response).

In this connection, when the command signal acquired by demodulating the radio-wave signals received from the external device through the antenna section 180 is the NAK response (being the negative response representing that the data are not correctly received), the control section 101 of the information processing apparatus 100 controls the communicating section 160 to retransmit the radio-wave signals, modulated with the data communication finalizing command and having the predetermined frequency, (retransmission of the ENQ command).

Further, when the external device can receive the radio-wave signals sent from the external device and can demodulate the data communication finalizing command (enable of receiving the ENQ command), the controlling section of the external device determines that the ENQ command is correctly received. Then, at the time when the preparing operations to be conducted at the external device side are completed, the controlling section of the external device transmits the radio-wave signals modulated with the ACK response (being the transmission control character transmitted by the receiver as the affirmative response to the sender, representing that all of the transmitted data are correctly received and the preparation for receiving the next data is completed) to the information processing apparatus 100 (transmission of the ACK response).

At this time, if the information processing apparatus 100 can receives the radio-wave signals sent from the external device and can demodulate the ACK response (enable of receiving the ACK response), the control section 101 of the information processing apparatus 100 determines that the communication with the external device is established and the preparation at the external device side is already completed, and then, transmits the radio-wave signals, modulated with the data communication finalizing command and having the predetermined frequency, to the external device through the antenna section 180 (transmission of the data communication finalizing command).

In this connection, when the external device cannot receive the radio-wave signals modulated with the data communication finalizing command from the information processing apparatus 100 (disable of receiving the data), or cannot correctly demodulate the data communication finalizing command from the received radio-wave signals, the controlling section of the external device determines that the current reception is abnormal. Then, the controlling section sends the radio-wave signals, modulated with the NAK response (being the negative response representing that the data are not correctly received) and having a predetermined frequency, to the information processing apparatus 100 (transmission of the NAK response).

At this time, if the command signal acquired by demodulating the radio-wave signals sent from the external device through the antenna section 180 is the NAK response (being the negative response representing that the data are not correctly received), the control section 101 controls the communicating section 160, so as to retransmit the radio-wave signals modulated with the data communication finalizing command and having the predetermined frequency through the antenna section 180 (retransmission of the data communication finalizing command).

Further, when the external device can receive the radio-wave signals sent from the information processing apparatus 100 and can demodulate the data communication finalizing command (enable of receiving the data communication finalizing command), the controlling section of the external device determines that the data communication finalizing command is correctly received. Then, at the time when the preparing operations to be conducted at the external device side are completed, the controlling section of the external device transmits the radio-wave signals modulated with the ACK response (being a transmission control character transmitted by a receiver as an affirmative response to the sender, representing that all of the transmitted data are correctly received and the preparation for receiving the next data is completed) to the information processing apparatus 100 (transmission of the ACK response).

At this time, if the information processing apparatus 100 can receives the radio-wave signals sent from the external device and can demodulate the ACK response (enable of receiving the ACK response), the control section 101 of the information processing apparatus 100 determines that the communication with the external device, in respect to the data communication finalizing command, is established and the preparation, in respect to the data communication finalizing command, at the external device side is already completed. Then, the control section 101 transmits the radio-wave signals modulated with the EOT (END OF TRANSMISSION) command, being a transmission control character or bits used to indicate the conclusion of the processing concerning to this data communication finalizing command, to the external device (transmission of the EOT), so as to finalize the processing for this communication commencement request (phase (11) shown in FIG. 8). Incidentally, after that, if the processing for the communication commencement request should be implemented so as to conduct the same processing mentioned in the above, the information processing apparatus 100 returns to the phase (1) shown in FIG. 6.

On the other hand, when the external device can receive the radio-wave signals sent from the information processing apparatus 100 and can demodulate the EOT command (enable of receiving the EOT command), the controlling section of the external device determines that the data communication finalizing processing in communication with the information processing apparatus 100 is completed, and finalizes the processing for this data communication finalizing command (phase (12) shown in FIG. 8). Incidentally, after that, if the processing for the communication commencement request should be implemented so as to conduct the same processing mentioned in the above, the external device returns to the phase (2) shown in FIG. 6.

Although the data communicating operations between the information processing apparatus 100 and the external device have been described in the foregoing while referring to the state transition diagrams, the operations same as described in the foregoing can be conducted even when the positions of the information processing apparatus 100 and the external device are reversed to each other. Further, the operations same as described in the foregoing are also applicable for data communicating operations to be conducted between the information processing apparatus 100 and another information processing apparatus serving as a similar wearable device.

Figure 9:
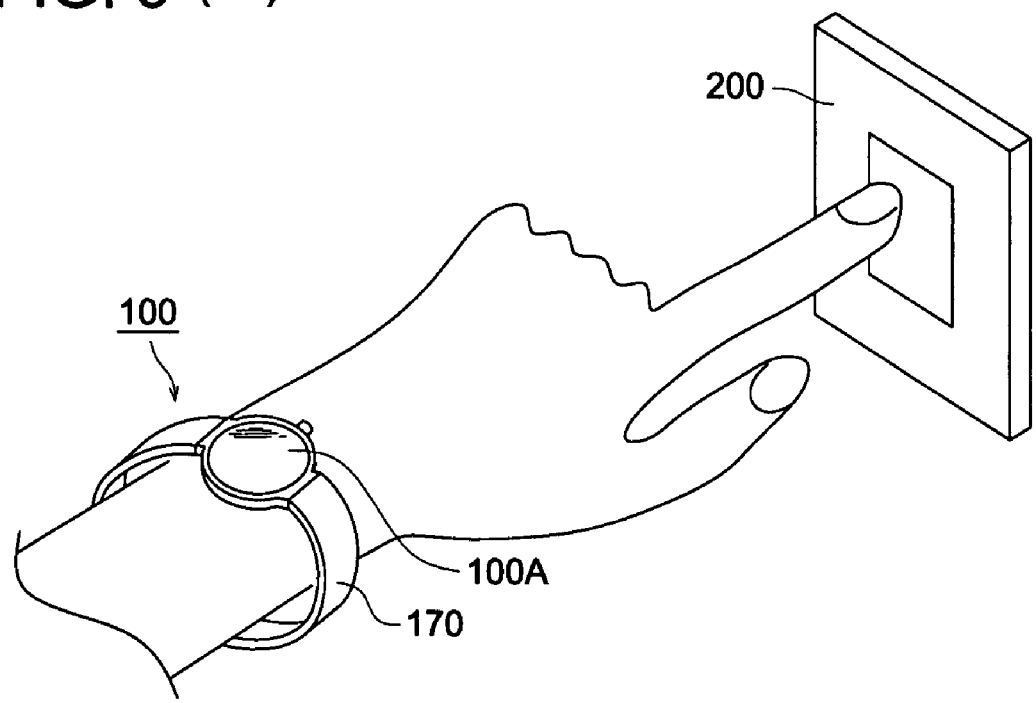
FIG. 9(a) and FIG. 9(b) show explanatory schematic diagrams indicating outer appearances of information processing apparatus 100 when using them.
Figure 9:
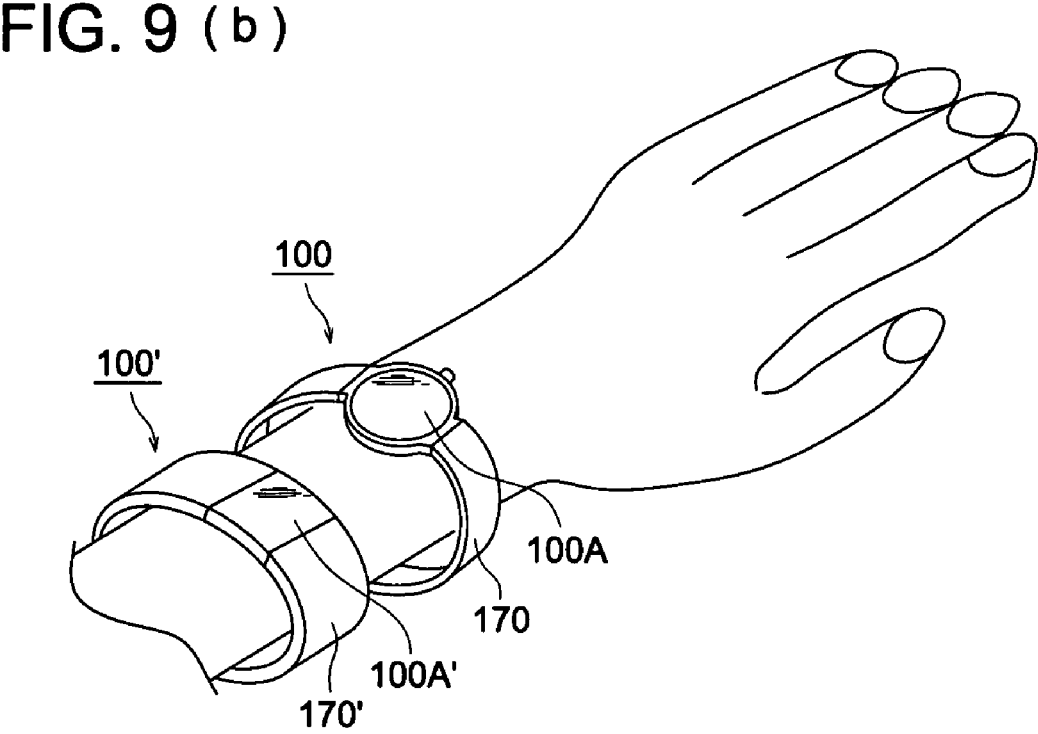

FIG. 9(*a*) shows an explanatory view indicating such a state that the information processing apparatus 100 and an external device 200 are close to each other. As shown in FIG. 9(*a*), the information processing apparatus 100 is fitted on the living body by making the wearing section 170 surround a part of the living body.

Further, since the wireless communication with the external device 200 is achieved through the antenna section 180, configured as a dipole antenna or a loop antenna and formed (or embedded) in the wearing section 170, it becomes possible to avoid a direct contact between the electrode and the surface of the living body when wearing it. Further, since the radio-wave signals propagate around the surface of the living body in the vicinity of the wearing section 170 worn on the living body, it becomes possible not only to reduce the divergence of the data towards the peripheral space, but also to conduct the communication, which is superior in the transmission efficiency.

Figure 10:
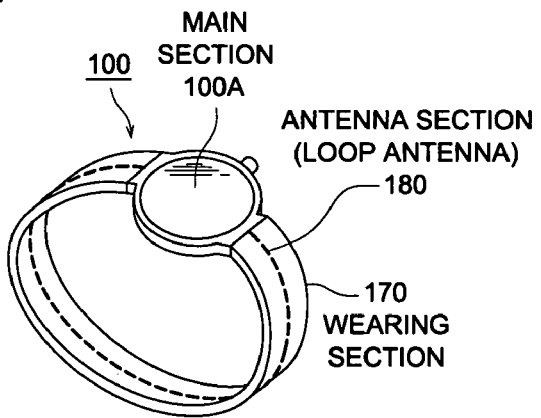
FIG. 10(a) and FIG. 10(b) show explanatory schematic diagrams indicating outer appearances and arrangements of antenna sections of information processing apparatus 100 embodied in the present invention.
Figure 10:
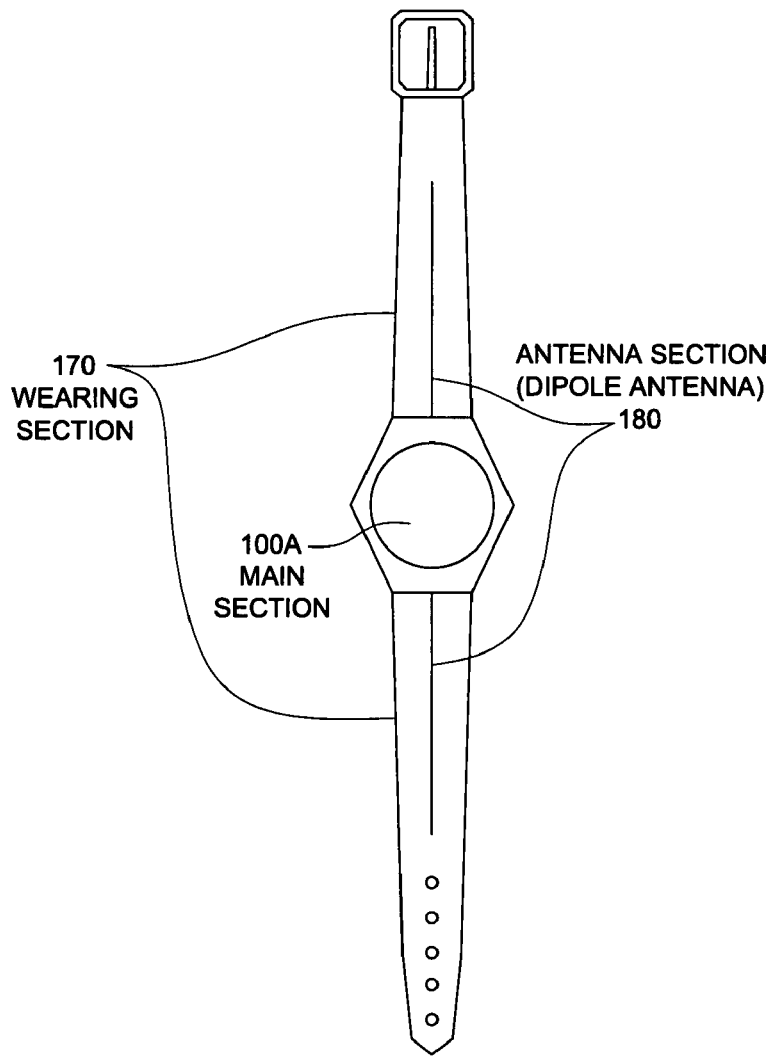

In this connection, when the wearing section 170 is formed in the closed annular shape as shown in FIG. 10(*a*), it is possible to form the antenna section 180 as the loop antenna (indicated by the broken line shown in FIG. 10(*a*)). Further, in the above case, it is also possible to form the antenna section 180 as the dipole antenna, instead of the loop antenna. Still further, when the wearing section 170 is formed in the open belt shape as indicated by the belt-type concrete example shown in FIG. 10(*b*), it is possible to form the antenna section 180 as the dipole antenna (indicated by the solid line shown in FIG. 10(*b*)). Still further, when the wearing section 170 is formed in any one of the one-side open rectangular shape, the character "C" shape and the character "U" shape, it is preferable that the wearing section 170 is formed as the dipole antenna as well.

In this connection, good communications can be achieved by setting the total length of the loop antenna at one when taking the wavelength $\lambda$, corresponding to the frequency of the radio-wave signals to be employed for both transmitting and receiving operations, into account. Further, good communications can be also achieved by setting the total length of the dipole antenna at $\frac{1}{2}\lambda$ (namely, the half wavelength dipole antenna), when taking the wavelength $\lambda$, corresponding to the frequency of the radio-wave signals to be employed for both transmitting and receiving operations, into account. Incidentally, it is also possible to employ a folded dipole antenna, in which two antenna elements are aligned in parallel, as the above-mentioned dipole antenna. Still further, with respect to the dipole antenna, since it is possible to shorten the length of the dipole antenna shorter than the total length of the wearing section 170, and accordingly, it becomes possible to select an arbitral frequency, the dipole antenna can be preferably employed for the neck strap, etc.

In this connection, when the loop antenna having a total length of 20 cm, which tunes to 1.5 GHz, is employed, it becomes possible to employ the radio-wave signals having a frequency higher than that employed in any conventional wearable devices, and accordingly, it becomes possible to achieve a high-speed transmission of more information than ever.

FIG. 9(b) shows an explanatory view indicating such a state that the information processing apparatus 100 and an information processing apparatus 100', serving as anther wearable device as the external device 200, are close to each other. As shown in FIG. 9(b), the information processing apparatus 100 is fitted on the living body as a wearable device by making the wearing section 170 surround a part of the living body. While, the information processing apparatus 100' is also fitted on the living body as a wearable device by making the wearing section 170' surround another part of the living body.

Further, since the wireless communications between the information processing apparatus 100 and the information processing apparatus 100' are implemented through the dipole antenna formed in the wearing section 170 or the antenna section 180 serving as the loop antenna, and the dipole antenna formed in the wearing section 170' or the antenna section 180' serving as the loop antenna, it becomes possible to avoid a direct contact between the electrode and the surface of the living body when wearing it. Further, since the radio-wave signals propagate around the surface of the living body in the vicinity of the wearing section 170 worn on the living body, it becomes possible not only to reduce the divergence of the data towards the peripheral space, but also to conduct the communication, which is superior in the transmission efficiency.

Still further, not only the example shown in FIG. 9(b), but also any combination of the wearing examples shown in FIG. 2(a), FIG. 2(b) and FIG. 2(c) are applicable as the case in which the wireless communications are conducted between plural wearable devices. In addition, since the electric contact directly onto the surface of the living body is not necessary in the information processing apparatus 100 embodied in the present invention, it becomes possible to conduct good communications without generating any problem, even when the information processing apparatus 100 is fitted on the clothes worn on the living body.

Still further, in the foregoing, the configuration shown in FIG. 9(b) is exemplified as the concrete example in which the wireless communications are conducted between plural wearable devices. However, according to the present invention, since the radio-wave signals propagate around the surface of the living body, good communications can be achieved, even when the plural wearable devices are fitted on separate parts of living body, such as a right hand and a left hand, a neck and a hand, an abdomen and a hand, a hand and a foot, etc., other than same parts of the living body (such as different positions of an arm, etc.).

In other words, it is applicable that the propagating direction of the radio-wave signals and the surface on which the directivity of the antenna resides not necessary coincide with each other.

Figure 11A:
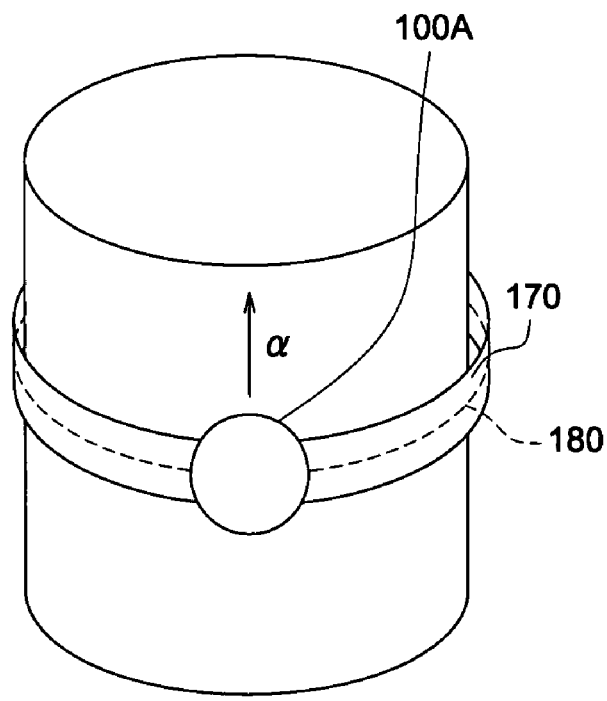
FIG. 11(a) and FIG. 11(b) show explanatory schematic diagrams indicating outer appearances of information processing apparatus 100 when using them.
Figure 11B:
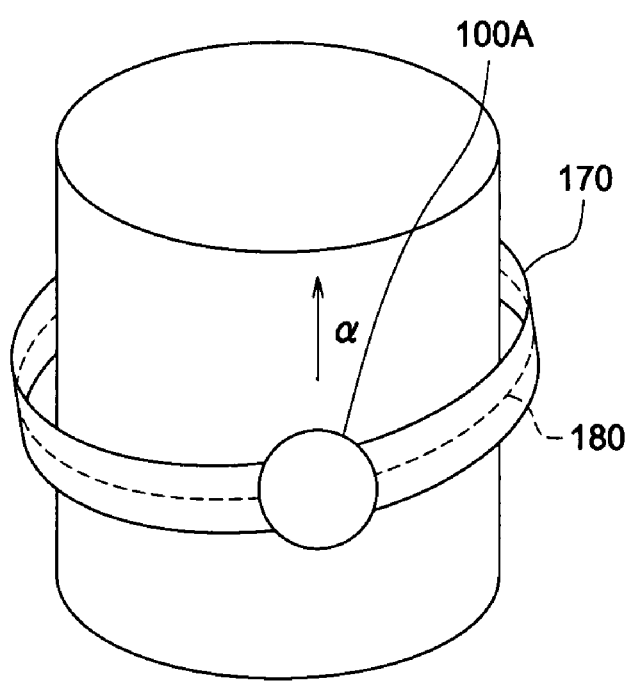

For instance, the wireless communications are conducted without generating any problem, either when the information processing apparatus 100 is fitted on the arm without generating any distortion of the wearing section 170 as shown in FIG. 11(a), or even when the information processing apparatus 100 is loosely fitted on the arm in such a manner that the wearing section 170 is slanted with respect to the arm as shown in FIG. 11(b). Wherein symbol α indicates the propagating direction of the radio-wave signals.

Further, when the information processing apparatus 100 is provided with the sensor section 150 and is fitted on the living body as the wearable device by making the wearing section 170 surround a part of the living body, it is possible for the sensor section 150 to detect biological information in respect to the detected living body (such as a body temperature, pulses, a blood pressure, an oxygen saturation level, a blood glucose value, etc.) or environmental information of the peripheral space (such as an ambient temperature, a humidity, an air pressure, height information, positional information, traffic information of the peripheral space, etc.).

Successively, the detected results in regard to abovementioned items are processed by the control section 101 serving as the information processing section, so as to transmit the processed data to the external device through the communicating section 160 and the antenna section 180. As a result, since the radio-wave signals propagate around the surface of the living body in the vicinity of the wearing section worn on the living body, it becomes possible not only to reduce the divergence of the data, including the biological information and the environmental information, towards the peripheral space, but also to conduct the communication, which is superior in the transmission efficiency.

Further, in the concrete example described in the foregoing, the wristwatch, the necklace, the ring, etc. are exemplified as the information processing apparatus 100. In addition to the above, any one of a head mount display, a headphone, a digital camera, various kinds of portable terminal devices, etc. can configure the information processing apparatus 100 incorporating the information processing section. In such the configuration, the wearing section 170 serves as a wearable material, such as various kinds of belts, eyeglasses, a frame of head mount display, a head band, a neck band, a wrist band, a hand strap, a neck strap, etc., which makes it possible to wear the information processing apparatus 100 on the living body by surrounding a part of the living body (human body). Further, the antenna section 180 is formed on the surface of or inside the wearing section 170, or the wearing section 170 itself is formed as the antenna section 180.

In the above configuration, since the information processing apparatus 100, serving as the wearable apparatus, is worn on the living body, and since the wireless communication with the external device is achieved through the antenna section 180, configured as a dipole antenna or a loop antenna, it becomes possible to avoid a direct contact between the electrode and the surface of the living body when wearing it. Further, since the radio-wave signals propagate around the surface of the living body in the vicinity of the wearing section 170 worn on the living body, it becomes possible not only to reduce the divergence of the data towards the peripheral space, but also to conduct the communication, which is superior in the transmission efficiency. Further, since the radio-wave signals propagate around the surface of the living body in the vicinity of the wearing section 170 worn on the living body to conduct the wireless communication with the external device, a little amount of the radio-wave signals modulated by the data diverges around the peripheral space, and accordingly, it becomes possible to conduct communicating operations, which consume a relatively small amount of electric power, compared to that consumed in the conventional apparatus. Therefore, it becomes possible to obtain an effect of reducing the power dissipation of the information processing apparatus 100.

Second Embodiment

Figure 12:
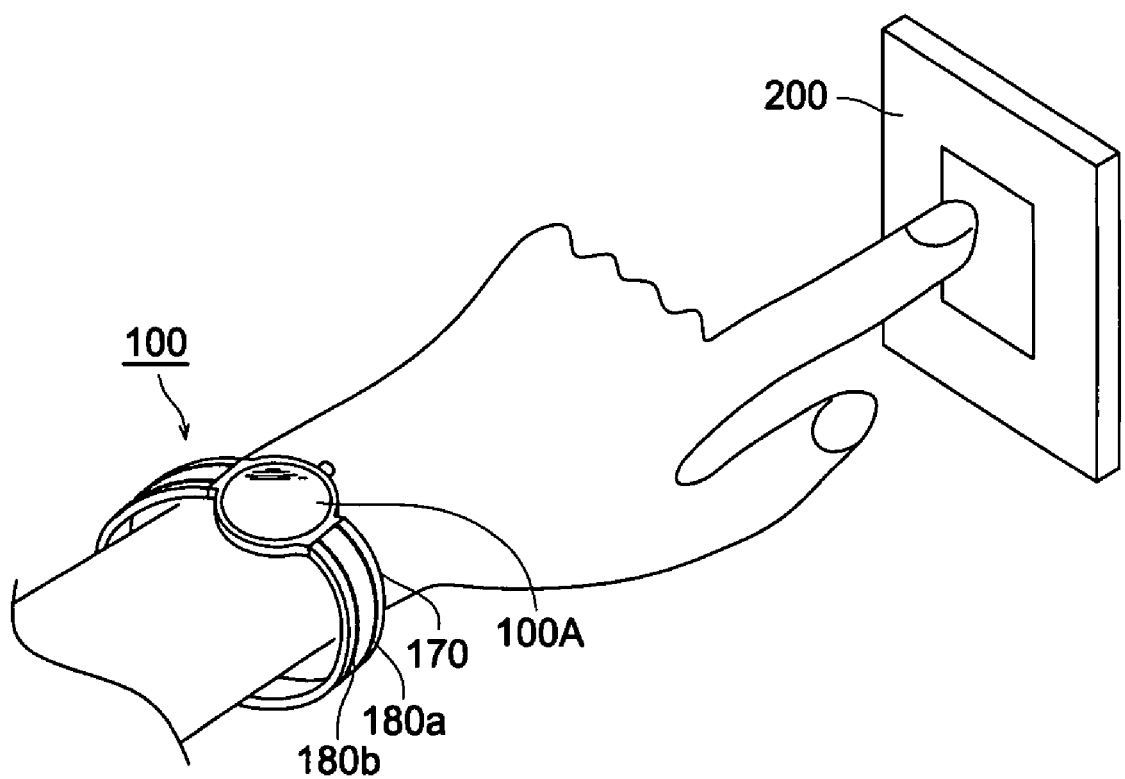
FIG. 12 shows explanatory schematic diagrams indicating outer appearances and arrangements of antenna sections of information processing apparatus 100 embodied in the present invention.

FIG. 12 shows an explanatory view indicating such a state that the information processing apparatus 100 and the external device 200 are close to each other. Where, the propagating direction of the radio-wave signals is directed to the position at which the external device resides, namely, the position pointed by the fingertip of the living body.

Accordingly, if directivity is given to the antenna section 180, a good communicating result can be obtained. For instance, by making an element 180a serve as a radiator, while by making an element 180b serve as a reflector, it becomes possible to direct the directivity towards the external device 200, resulting in a little waste divergence of the data and the communication, which is superior in the transmission efficiency. Further, since the radio-wave signals propagate towards the external device on the surface of the living body on which the wearing section 170 is worn, so as to conduct the wireless communication with the external device, a little amount of the radio-wave signals modulated by the data diverges around the peripheral space, and accordingly, it becomes possible to conduct communicating operations, which consume a relatively small amount of electric power, compared to that consumed in the conventional apparatus. Therefore, it becomes possible to obtain an effect of reducing the power dissipation of the information processing apparatus 100. Conversely, by making an element 180b serve as a radiator, while by making an element 180a serve as a reflector, it is possible to obtain the effects same as the above, as well.

Further, when the wireless communications are conducted between plural wearable devices, by directing the directivities of the antenna sections 180 of the plural wearable devices so as to coincide them with each other, it becomes possible to securely conduct the wireless communications consuming a little transmission power without generating any waste.

Although the operations of the two-element loop antenna or the two-element Yagi antenna have been described in the foregoing, still better results can be obtained when a number of elements is equal to or greater than three elements. Incidentally, in order to prevent the directivity from setting it at the reverse direction when wearing the information processing apparatus 100 on the opposite hand, it is desirable that a kind of symbol indicating the existence of the directivity is attached to any one of the main section 100A and the wearing section 170 of the information processing apparatus 100.

Further, it is also possible to change the directivity of the antenna, by changing the power feed for the antenna section 180, or by selecting specific elements to be currently employed for the antenna section 180 from a plurality of elements provided in advance, by changing the settings of the wearable device from the operating section. Incidentally, when the directivity of the antenna section 180 is changed, it is desirable that a kind of message indicating the existence of the directivity and its direction is displayed on the display section.

Other Embodiment

In each of the embodiments described in the foregoing, although the human body is exemplified as the living body serving as the transmission path through which the data communicating operations are conducted, it is needless to say that a living body, such as an animal, a plant, etc., other than the human body can be also employed as the transmission path for the wearable devices.

Further, in each of the embodiments described in the foregoing, although the human body is exemplified as the living body serving as the transmission path through which the data communicating operations are conducted, since the artificial materials, such as an artificial limb, an orthosis, an outfit, etc., conform to the living body, it is also possible to employ such the artificial materials as the transmission path for the wearable devices.

According to the present invention, the following effects can be attained.

(1) The information processing section is fitted on the living body by making the wearing section equipped with the antenna section surround a part of the living body. In this state, the wireless communication with an external device is implemented by transmitting data, processed by the information processing section, to the external device through the antenna section, or by feeding data, received from the external device through the antenna section, into the information processing section. In this connection, since the information processing apparatus is worn on the living body by making the wearing section surround a part of the living body, and the wireless communication with the external device is implemented through the antenna section serving as either a loop antenna or a dipole antenna, it becomes possible to conduct such the communication that makes it possible not only to reduce the divergence of data toward the peripheral spaces, but also to eliminate the electrode to be contacted to the surface of the living body when wearing it, and further, that is superior in the transmitting efficiency.

(2) The wearing section, equipped with the antenna section, is formed in a closed annulus shape. In this connection, since the information processing apparatus, serving as a wearable device, is worn on the living body by making the annulus-shaped wearing section surround a part of the living body, and the wireless communication with the external device is implemented through the antenna section serving as either a loop antenna or a dipole antenna, the radio-wave signals propagate in the vicinity of the surface of the living body on which the wearing section is fitted, and accordingly, it becomes possible to conduct such the communication that makes it possible to reduce the divergence of data toward the peripheral spaces, and further, that is superior in the transmitting efficiency.

(3) The wearing section is formed in any one of a one-side open rectangular shape, a character "C" shape and a character "U" shape. In this connection, since the information processing apparatus, serving as a wearable device, is worn on the living body by making the wearing section, formed in any one of a one-side open rectangular shape, a character "C" shape and a character "U" shape, surround a part of the living body, and the wireless communication with the external device is implemented through the dipole antenna equipped in this annulus-shaped wearing section, the radio-wave signals propagate in the vicinity of the surface of the living body on which the wearing section is fitted, and accordingly, it becomes possible to conduct such the communication that makes it possible to reduce the divergence of data toward the peripheral spaces, and further, that is superior in the transmitting efficiency.

(4) The information processing apparatus is further provided with the sensor to detect the living body information in regard to the living body or the environmental information in regard to the peripheral space. Both the living body information and the environmental information, detected by the sensor, are processed in the information processing section, so as to transmit processed data to the external device through the communication section and the antenna section. In this connection, the information processing apparatus, serving as a wearable device, is worn on the living body by making the wearing section surround a part of the living body, and at this time, both the living body information and the environmental information, detected by the sensor, are processed in the information processing section, and then, the processed data are transmitted to the external device through the communication section and the antenna section. As a result, since the radio-wave signals propagate in the vicinity of the surface of the living body on which the wearing section is fitted, it becomes possible to conduct such the communication that makes it possible to reduce the divergence of data toward the peripheral spaces, and further, that is superior in the transmitting efficiency.

(5) The information processing apparatus, serving as a wearable device, is worn on the living body by making the wearing section surround a part of the living body, and at this time, the data transmitting operations are conducted between the information processing apparatus and the other information processing apparatus, both of which are worn on the same living body. As a result, since the antenna section is incorporated in the wearing section, and the radio-wave signals propagate in the vicinity of the surface of the living body on which the wearing section is fitted, it becomes possible to conduct such the communication that makes it possible to reduce the divergence of data toward the peripheral spaces, and further, that is superior in the transmitting efficiency, between the information processing apparatus and the other information processing apparatus, both of which are worn on the same living body.

(6) The information processing apparatus is incorporated into any one of a wrist watch, a head mount display, a headphone, a digital camera and various kinds of portable terminal devices, and worn on the living body by employing the wearing section. In this connection, any one of a wrist watch, a head mount display, a headphone, a digital camera, various kinds of portable terminal devices is configured as the information processing apparatus incorporating the information processing section, and is worn on the living body by employing the wearing section. Since the wireless communication with the external device is implemented through the antenna section serving as either a loop antenna or a dipole antenna, it becomes possible to conduct such the communication that makes it possible not only to reduce the divergence of data toward the peripheral spaces, but also to eliminate the electrode to be contacted to the surface of the living body when wearing it, and further, that is superior in the transmitting efficiency.

While the preferred embodiments of the present invention have been described using specific term, such description is for illustrative purpose only, and it is to be understood that changes and variations may be made without departing from the spirit and scope of the appended claims.

The invention claimed is:

1. An information processing apparatus, comprising:
an information processing section to conduct various kinds of information processing;
a wearing section to surround a part of a living body, so as to make the information processing section wearable onto the living body;
an antenna section that serves as one of a loop antenna and a dipole antenna, integrally formed in the wearing section; and
a communicating section to at least one of transmit data, processed in the information processing section, to an external device through the antenna section, and receive data, sent from the external device and to be fed into the information processing section, in order to implement wireless communication with the external device;
wherein data transmitting operations are conducted between the information processing apparatus and another information processing apparatus, both of which are worn on the same living body.

2. The information processing apparatus of claim 1, wherein the wearing section is formed in a closed annulus shape.

3. The information processing apparatus of claim 1, wherein the wearing section is formed in any one of a one-side open rectangular shape, a character "C" shape and a character "U" shape.

4. An information processing apparatus comprising:
an information processing section to conduct various kinds of information processing;
a wearing section to surround a part of a living body, so as to make the information processing section wearable onto the living body;
an antenna section that serves as one of a loop antenna and a dipole antenna, integrally formed in the wearing section;
a communicating section to at least one of transmit data, processed in the information processing section to a external device through the antenna section, and receive data, sent from the external device and to be fed into the information processing section, in order to implement wireless communication with the external device; and
a sensor to detect at least one of living body information in regard to the living body and environmental information in regard to a peripheral space;
wherein the at least one of the living body information and the environmental information, detected by the sensor, are processed in the information processing section, and the processed data is transmitted to the external device through the communication section and the antenna section.

* * * * *